(12) United States Patent
Teoh et al.

(10) Patent No.: US 8,940,011 B2
(45) Date of Patent: Jan. 27, 2015

(54) COMPOSITE DETACHMENT MECHANISMS

(75) Inventors: Clifford Teoh, Los Altos, CA (US); Francis Tang, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1108 days.

(21) Appl. No.: 12/584,651

(22) Filed: Sep. 9, 2009

(65) Prior Publication Data

US 2010/0063572 A1 Mar. 11, 2010

Related U.S. Application Data

(60) Provisional application No. 61/191,456, filed on Sep. 9, 2008.

(51) Int. Cl.
*A61M 29/00* (2006.01)
*A61B 17/12* (2006.01)

(52) U.S. Cl.
CPC ..... *A61B 17/12022* (2013.01); *A61B 17/12113* (2013.01); *A61B 17/1214* (2013.01); *A61B 2017/12068* (2013.01)
USPC ....................................................... 606/200

(58) Field of Classification Search
USPC .......... 606/108, 191, 194, 198, 200; 623/1.11
See application file for complete search history.

(56) References Cited

U.S. PATENT DOCUMENTS

| | | | |
|---|---|---|---|
| 3,174,851 A | 3/1965 | Buehler | |
| 3,351,463 A | 11/1967 | Rozner | |
| 3,753,700 A | 8/1973 | Harrison et al. | |
| 4,735,201 A | 4/1988 | O'Reilly | |
| 4,739,768 A | 4/1988 | Engelson | |
| 4,994,069 A | 2/1991 | Ritchart et al. | |
| 5,108,407 A | 4/1992 | Geremia et al. | |
| 5,122,136 A | 6/1992 | Guglielmi et al. | |
| 5,226,911 A | 7/1993 | Chee et al. | |
| 5,354,295 A | 10/1994 | Guglielmi et al. | |
| 5,582,619 A | 12/1996 | Ken | |
| 5,759,161 A | 6/1998 | Ogawa et al. | |
| 5,833,705 A | 11/1998 | Ken et al. | |
| 5,846,210 A | 12/1998 | Ogawa et al. | |
| 5,853,418 A | 12/1998 | Ken et al. | |
| 5,935,145 A | 8/1999 | Villar et al. | |
| 5,944,733 A | 8/1999 | Engelson | |
| 5,976,131 A | 11/1999 | Guglielmi et al. | |
| 6,004,338 A | 12/1999 | Ken et al. | |
| 6,013,084 A | 1/2000 | Ken et al. | |
| 6,033,423 A | 3/2000 | Ken et al. | |
| 6,059,779 A | 5/2000 | Mills | |

(Continued)

FOREIGN PATENT DOCUMENTS

EP 0992220 4/2000
EP 0 992 220 B1 12/2003

(Continued)

OTHER PUBLICATIONS

International Search Report and the Written Opinion for International Application No. PCT/US2009/005059 filed Sep. 9, 2009, search report mailed Nov. 18, 2009 (14 pages).

*Primary Examiner* — Katherine M Shi
(74) *Attorney, Agent, or Firm* — Kacvinsky Daisak Bluni PLLC

(57) ABSTRACT

Described herein are composite detachment mechanisms for implantable devices and assemblies comprising these devices. Also provided are methods of using the detachment mechanisms and assemblies.

15 Claims, 3 Drawing Sheets

(56) References Cited

U.S. PATENT DOCUMENTS

| | | | |
|---|---|---|---|
| 6,059,815 A | 5/2000 | Lee et al. | |
| 6,113,622 A | 9/2000 | Hieshima | |
| 6,179,857 B1 | 1/2001 | Diaz et al. | |
| 6,193,728 B1 | 2/2001 | Ken et al. | |
| 6,277,126 B1 | 8/2001 | Barry et al. | |
| 6,280,457 B1 | 8/2001 | Wallace et al. | |
| 6,287,318 B1 | 9/2001 | Villar et al. | |
| 6,299,627 B1 | 10/2001 | Eder et al. | |
| 6,409,721 B1 | 6/2002 | Wheelock et al. | |
| 6,425,893 B1 | 7/2002 | Guglielmi | |
| 6,533,801 B2 | 3/2003 | Wallace et al. | |
| 6,585,754 B2 | 7/2003 | Wallace et al. | |
| 6,589,236 B2 | 7/2003 | Wheelock et al. | |
| 6,620,152 B2 | 9/2003 | Guglielmi | |
| 6,623,493 B2 | 9/2003 | Wallace et al. | |
| 6,743,251 B1 | 6/2004 | Eder | |
| 7,020,516 B2 | 3/2006 | Flock et al. | |
| 2004/0247849 A1* | 12/2004 | Truckai | 428/292.1 |
| 2005/0113864 A1* | 5/2005 | Gandhi et al. | 606/200 |
| 2006/0036280 A1* | 2/2006 | French et al. | 606/200 |
| 2006/0200192 A1* | 9/2006 | Fitz et al. | 606/200 |
| 2006/0206140 A1* | 9/2006 | Shaolian et al. | 606/200 |
| 2006/0271086 A1 | 11/2006 | Ramzipoor et al. | |
| 2006/0271097 A1 | 11/2006 | Ramzipoor et al. | |
| 2007/0032862 A1* | 2/2007 | Weber et al. | 623/1.34 |

FOREIGN PATENT DOCUMENTS

| | | |
|---|---|---|
| WO | WO 02/051460 A2 | 7/2002 |
| WO | 02/096301 | 12/2002 |
| WO | WO 02/096273 A2 | 12/2002 |
| WO | WO 03/051444 A1 | 6/2003 |
| WO | 2006/024040 | 3/2006 |

* cited by examiner

COMPOSITE DETACHMENT MECHANISMS

CROSS-REFERENCE TO RELATED APPLICATIONS

This application claims the benefit of U.S. provisional patent application No. 61/191,456, filed Sep. 9, 2008, the disclosure of which is incorporated by reference in its entirety for all purposes.

FIELD OF THE INVENTION

This invention relates to composite detachment mechanisms for implantable devices.

BACKGROUND

An aneurysm is a dilation of a blood vessel that poses a risk to health from the potential for rupture, clotting, or dissecting. Rupture of an aneurysm in the brain causes stroke, and rupture of an aneurysm in the abdomen causes shock. Cerebral aneurysms are usually detected in patients as the result of a seizure or hemorrhage and can result in significant morbidity or mortality.

There are a variety of materials and devices which have been used for treatment of aneurysms, including platinum and stainless steel microcoils, polyvinyl alcohol sponges (Ivalone), and other mechanical devices. For example, vaso-occlusion devices are surgical implements or implants that are placed within the vasculature of the human body, typically via a catheter, either to block the flow of blood through a vessel making up that portion of the vasculature through the formation of an embolus or to form such an embolus within an aneurysm stemming from the vessel. One widely used vaso-occlusive device is a helical wire coil having windings that may be dimensioned to engage the walls of the vessels. (See, e.g., U.S. Pat. No. 4,994,069 to Ritchart et al.). Variations of such devices include polymeric coatings or attached polymeric filaments have also been described. See, e.g., U.S. Pat. Nos. 5,226,911; 5,935,145; 6,033,423; 6,280,457; 6,287,318; and 6,299,627. In addition, coil designs including stretch-resistant members that run through the lumen of the helical vaso-occlusive coil have also been described. See, e.g., U.S. Pat. Nos. 5,582,619; 5,833,705; 5,853,418; 6,004,338; 6,013,084; 6,179,857; and 6,193,728.

Typically, implantable devices include a detachment mechanism in order to be released from the deployment mechanism (e.g., attached wire). Several classes of techniques have been developed to enable more accurate placement of implantable devices within a vessel. One class involves the use of electrolytic means to detach the vasoocclusive member from the pusher. Electrolytic coil detachment is disclosed in U.S. Pat. Nos. 5,122,136; 5,354,295; 6,620,152; 6,425,893; and 5,976,131, all to Guglielmi et al., describe electrolytically detachable embolic devices. U.S. Pat. No. 6,623,493 describes vaso-occlusive member assembly with multiple detaching points. U.S. Pat. Nos. 6,589,236 and 6,409,721 describe assemblies containing an electrolytically severable joint. U.S. Patent Publication No. 20060271097A1 describes interlocking loop detachment junctions made of metal in which the loop proximal to the implantable device is degraded by the application of energy. U.S. Patent Publication No. 20060271086A1 describes flexible detachment junctions formed by covering the implantable device and a delivery device with an articulating degradable polymer.

Other forms of energy are also used to sever sacrificial joints that connect pusher and vasoocclusive member apparatus. Sacrificial connection member, preferably made from polyvinylacetate (PVA), resins, polymers, or shape memory alloys, can be used to join a conductive wire to a retention member. See, U.S. Pat. Nos. 5,759,161 and 5,846,210. Upon heating by a monopolar high frequency current, the sacrificial connection member melts, severing the wire from the retention member.

U.S. Pat. No. 5,944,733 describes application of radiofrequency energy to sever a thermoplastic joint and U.S. Pat. No. 6,743,251 describes polymeric detachment joints that are severed by the application of low frequency energy or direct current. U.S. Pat. No. 6,346,091 describes a wire detachment junction that is severed by application of vibrational energy.

In U.S. Pat. No. 4,735,201 to O'Reilly, an optical fiber is enclosed within a catheter and connected to a metallic tip on its distal end by a layer of hot-melt adhesive. The proximal end of the optical fiber is connected to a laser energy source. When endovascularly introduced into an aneurysm, laser energy is applied to the optical fiber, heating the metallic tip so as to cauterize the immediately surrounding tissue. The layer of hot-melt adhesive serving as the bonding material for the optical fiber and metallic tip is melted during this lasing, but the integrity of the interface is maintained by application of back pressure on the catheter by the physician. When it is apparent that the proper therapeutic effect has been accomplished, another pulse of laser energy is then applied to once again melt the hot-melt adhesive, but upon this reheating the optical fiber and catheter are withdrawn by the physician, leaving the metallic tip in the aneurysm as a permanent plug. See, also U.S. Pat. No. 6,277,126.

Other methods for placing implantable devices within the vasculature utilize heat releasable bonds that can be detached by using laser energy (see, U.S. Pat. No. 5,108,407). EP 0 992 220 describes an embolic coil placement system which includes conductive wires running through the delivery member. When these wires generate sufficient heat, they are able to sever the link between the embolic coil and the delivery wires. Further, U.S. Pat. No. 6,113,622 describes the use of fluid pressure (e.g., hydraulics) to detach an embolic coil.

However, there remains a need for composite detachment mechanisms as described herein.

SUMMARY

Described herein are thermally activated composite detachment mechanisms made of a polymer that melts upon thermal activation and a conductive material. When sufficient energy (e.g., electrical/thermal) is applied (via the conductive material) to the detachment mechanism, the polymer melts to an extent that the attached implantable device is released from the delivery mechanism into the vasculature.

In certain aspects, provided herein is an assembly comprising: an implantable device, and a composite detachment mechanism comprising a polymer and one or more conductive materials, wherein the composite detachment mechanism is engaged (directly or indirectly) with the implantable device until sufficient thermal energy is applied to the detachment mechanism to allow disengagement of the implantable device to take place. The one or more conductive materials may be coated on the polymer and/or the polymer may be coated onto the one or more conductive materials.

In any of the assemblies described herein, the polymer may comprise a low melt polymer such as polyethylene (PE), poly-L-lactic acid (PLLA), polyglycolic acid (PGA), polyvinyl alcohol (PVA) and combinations thereof. Similarly, the assemblies may comprise one or more layers of the conductive material, which may be for example, a metal (e.g., nickel, iron chromium, tin, gold, platinum or combinations thereof). In certain embodiment, the assembly comprises a single layer of one or more conductive materials. In other embodiments, the assembly comprises multiple layers of two or more conductive materials In yet another aspect, any of the assemblies described herein may further comprise an energy source (e.g., source of electrical or thermal energy) operably connected to one or more electrodes in direct or indirect contact with the conductive material. In certain embodiments, the energy source comprises two electrodes, wherein the distal end of the electrodes comprise ring structures and wherein the ring structures directly contact the conductive coating of the composite detachment mechanism. The electrodes may contact a fabricated electrode assembly, for example a fabricated electrode assembly comprising an insulating layer positioned between two conductive layers; and a melt receptacle orifice spanning the insulating layer and at least part of the conductive layers, wherein the conductive material of the composite detachment mechanism contacts the two conductive layers when engaged with the implantable device.

In a still further aspect, any of the assemblies described herein may further comprise a delivery device, for example, a catheter, a guide wire and/or a continuous conduit.

Any of assemblies described herein may further comprise one or more insulating materials, for example a single layer of insulating material(s) or multiple continuous or discontinuous layers of insulating material(s).

In any of the assemblies described herein, the implantable device may comprise a vaso-occlusive device, for example a vaso-occlusive coil or a tubular braid. The vaso-occlusive device may comprise one or more metals and/or one or more polymers. In certain embodiments, the device comprises a metal selected from the group consisting of gold, platinum, tungsten, nickel, titanium and alloys thereof. In other embodiment, the vaso-occlusive device comprises a polymer, for example, the polymer is coated onto a metal vaso-occlusive device.

In another aspect, described herein is a method of occluding a body cavity, the method comprising introducing one or more of any of the implantable assemblies described herein into the body cavity. In certain embodiments, the method comprises the steps of introducing an implantable assembly as described herein into the body cavity; and applying sufficient energy to release the implantable device into the body cavity, thereby occluding the body cavity. In certain embodiments, the body cavity is an aneurysm.

These and other embodiments will readily occur to those of skill in the art in light of the disclosure herein.

DETAILED DESCRIPTION

Figure 1A:
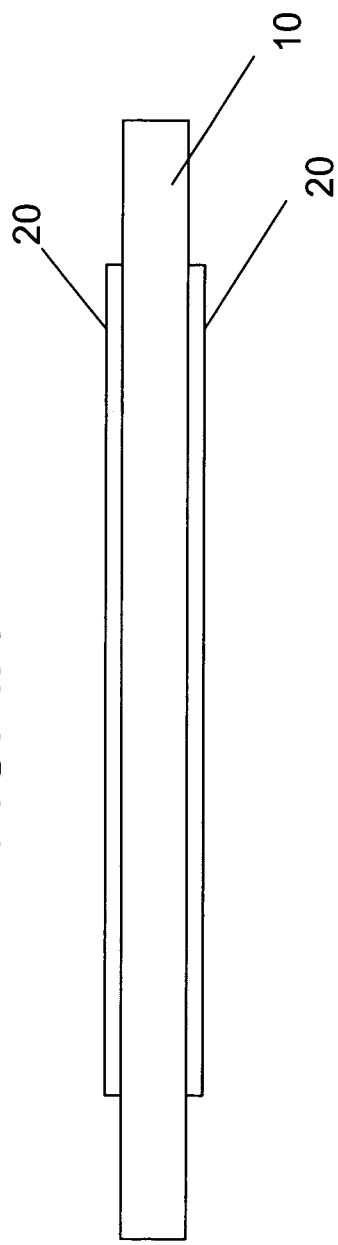
FIG. 1, panels A and B, are side views of exemplary assemblies comprising a thermally detachable composite detachment mechanism as described herein.

Composite detachment mechanisms for implantable devices and assemblies comprising these detachment mechanisms are described. The detachment mechanisms described herein find use in deploying vascular and neurovascular implants and are particularly useful in treating aneurysms, for example small-diameter, curved or otherwise difficult to access vasculature, for example aneurysms, such as cerebral aneurysms. Methods of making and using these detachment mechanisms and assemblies are also described.

All publications, patents and patent applications cited herein, whether above or below, are hereby incorporated by reference in their entirety.

It must be noted that, as used in this specification and the appended claims, the singular forms "a", "an", and "the" include plural referents unless the content clearly dictates otherwise.

The composite detachment mechanisms described herein include a meltable polymer and a conductive material. Upon application of energy (electrical/thermal) via the conductive material, the polymer is degraded (melted) and the implantable device detached from the delivery device.

Any polymer can be used in the detachment mechanisms described herein, including, but not limited to, polyethylene (PE), poly-L-lactic acid (PLLA), polyglycolic acid (PGA), polyvinyl alcohol (PVA), as well as other degradable polymers known to those of skill in the art. In a preferred embodiment, the polymer element comprises a low-melting polymer such as PE. The polymer element may comprise a single filament and/or multiple filaments that are woven, braided and/or twisted around each other.

Similarly, any conductive material can be used with the polymeric element in the composite detachment mechanisms described herein. In certain embodiments, the conductive material comprises a metal, for example nickel, iron, tin, chromium, gold, platinum, or combinations thereof (e.g., NiCr, NiCrFe, SnO, Au and/or Pt). In certain embodiments, two or more layers of the same or different materials are used to form the conductive material.

The conductive material may be combined with the polymer in any suitable fashion, including but not limited to, dip coating (continuous or discontinuous), sputter-coating, plating, use of adhesives, etc. In certain embodiments, the polymer surrounds (e.g. is coated onto) a conductive material so as to form a meltable polymeric junction (e.g., the substrate conductive material does not extend through the meltable junction). In other embodiments, the conductive material is coated onto the polymeric substrate in a continuous region. The conductive material is selected such that passing a current through it results in heating to temperatures above the melting point of the polymeric element. At the point of melting, surface tension of the polymer melt will cause retraction and separation of the fiber into two separate pieces. Axially straining of the polymeric substrate (e.g., by operator pushing and/or pulling) may further facilitate the melting and separation effectiveness.

Delivery mechanisms (e.g., catheter, delivery tube, guide wire systems, etc.) that allow for transmission of electrical energy are well known in the art. Catheters with electrodes in the walls are described for example in U.S. Pat. Nos. 6,059,779 and 7,020,516. Electrodes may also be transmitted through the lumen of the delivery mechanism. For example, bi-polar electrodes and/or anodes alone or twisted with a core wire cathode can also be used to supply current to the degradable detachment mechanism.

Depicted in the appended drawings are exemplary embodiments of the present invention in which the implantable device is depicted as an embolic device. It will be appreciated that the drawings are for purposes of illustration only and that other implantable devices can be used in place of embolic devices, for example, stents, filters, and the like. Furthermore, although depicted in the Figures as embolic coils, the embolic devices may be of a variety of shapes or configuration including, but not limited to, braids, wires, knits, woven structures, tubes (e.g., perforated or slotted tubes), injection-molded devices and the like. See, e.g., U.S. Pat. No. 6,533,801 and International Patent Publication WO 02/096273. It will also be appreciated that the assemblies can have various configurations as long as the required flexibility is present.

Figure 1B:
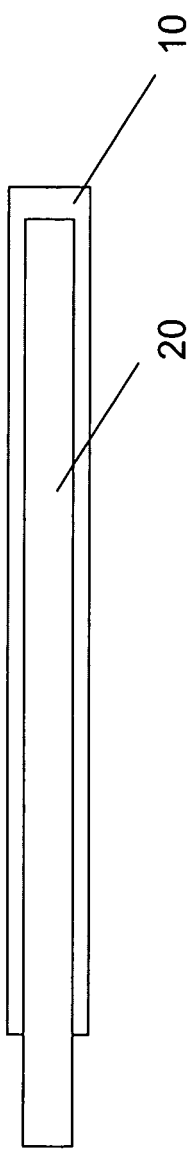

FIG. 1, panels A and B, are side views of exemplary composite detachment mechanism as described herein comprising at least one polymer and at least one conductive material. FIG. 1A is a side and view of an exemplary polymer substrate 10 coated with a conductive material 20. As shown, the coating can be continuous over a particular portion of the polymer. FIG. 1B shows the reverse orientation in which a conductive material substrate 20 is coated with a meltable polymer 10.

Figure 2:
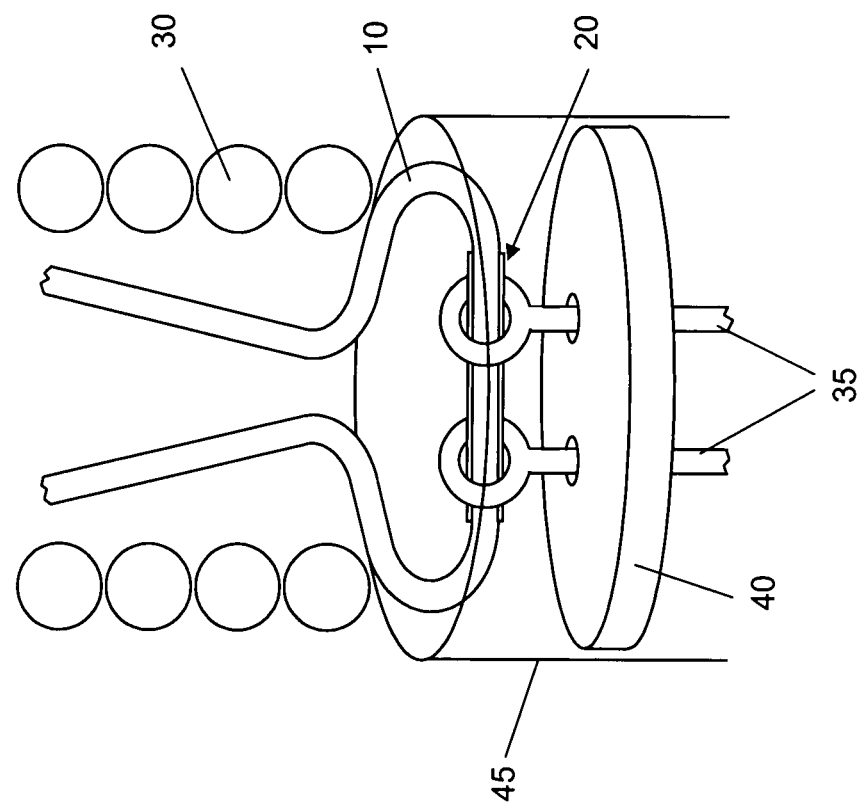
FIG. 2 is an overview and partial cross-section of an exemplary assembly as described herein comprising a composite thermally detachable mechanism.

FIG. 2 shows an exemplary assembly as described herein. The implantable device 30 is depicted as a vaso-occlusive coil (cross-section view). The detachment mechanism comprises polymer strands 10 and a conductive material 20 coating a portion of the polymer 10. Also shown are electrodes 35, delivery device 45 and optional insulating electrode spacer 40.

In the embodiment depicted, electrodes 35 are configured as rings that contact the conductive material 20. It will be apparent that other configurations are also possible including, but not limited to, linear electrodes that terminate at (and are optionally attached to) the conductive material 20 of the detachment mechanism, hooked shaped electrodes, combinations of rings, hooks, linear electrodes and the like. Furthermore, configurations in which the electrodes are configured to elevate and isolate the composite detachment mechanism and resultant melt from other surfaces is preferred to help ensure better separation.

Figure 3:
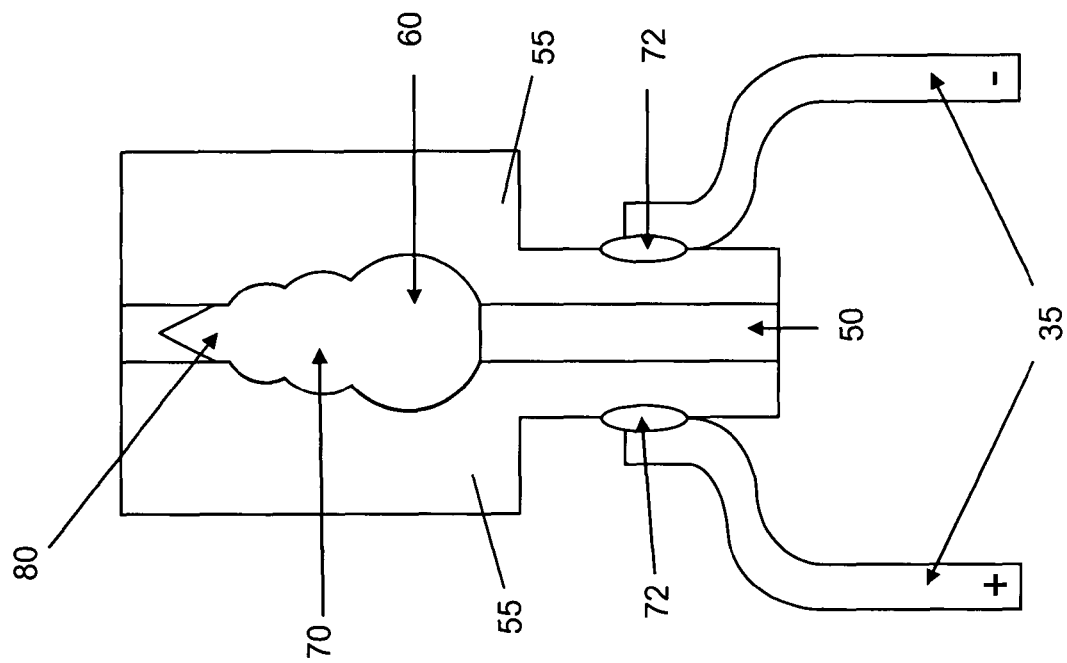
FIG. 3 is a cross-section view of a microfabricated electrode assembly.

FIG. 3 shows a cross-section of an alternative embodiment in which the electrode assembly is fabricated (micro-fabricated) to incorporate an insulating layer 50, which allows electrical isolation between the two contacts. In the embodiment shown, the microfabricated assembly comprises two electrodes (conductive wires) 35, each of which are electrically connected 72 to each of the two conductive layers 55. The electrodes can be connected to the conductive layers in any way including, but not limited, to soldering, adhesives, etc. Optionally, the composite detachment mechanism (polymer coated with conductive material) can be threaded through fiber threading cavity 60 and pulled taught to fit within the detach fiber cavity 70 such that the conductive coating 20 of the composite detachment mechanism bridges the distal gap and is in contact with both the conductive layers 55 of the fabricated electrode assembly.

Upon application of heat (electrical energy), the polymer fiber 10 of the composite detachment mechanism will melt into the melt receptacle 80 and/or into the fiber threading cavity 60, which function as reservoirs to contain the melted polymer to prevent potential shorting of the conductive layers by the melt products. The melt receptacle 80 and threading cavity 60 also provide additional surface area, which reduces or eliminates shorting in that the melted polymer has to coat an entire continuous area bridging both electrode gaps before a short occurs. The size and surface area of the melt receptacle can readily be determined and adjusted by the skilled artisan depending on various factors, for example, the thickness and volume of the polymer 10 to be melted.

In any of the embodiments described herein, one or more, preferably two, electrodes are typically employed. The polymer 10 component of the composite detachment mechanism is preferably attached to the implantable device in such a way that when the composite portion of the detachment mechanism is melted the device 10 and attached (severed) polymer 10 is released into the desired sites.

Thus, conductor element 35 will be any configuration and material that allows for delivery of energy to melt the polymer 10 in the conductive material-coated region of the polymeric detachment mechanism. For example, the conductor element may comprise a conductive material such as stainless steel, platinum, gold, etc that is formed into a ring around the composite detachment mechanism. Alternatively, the electrode may be fabricated with conductive and insulating layers as well as a melt receptacle as shown in FIG. 3. Furthermore, although shown in the Figures as positioned in the lumen of the delivery device, it will be apparent that the conductor element(s) 35 can be positioned in the sidewalls of the selected delivery device 45.

The assemblies may also include an energy source which is preferably connected to the electrodes exterior to the subject's vasculature. In addition, the assemblies may include one or more actuators which allow the operator to input the energy or to degrade (melt) the detachment mechanism when deployment of the implant 30 is desired.

With regard to particular materials used in the implantable devices and assemblies of the invention, it is to be understood that the implantable devices or assemblies may be made of a variety of materials, including but not limited to metals, polymers and combinations thereof, including but not limited to, stainless steel, platinum, kevlar, PET, carbothane, cyanoacrylate, epoxy, poly(ethyleneterephthalate) (PET), polytetrafluoroethylene (Teflon™), polypropylene, polyimide polyethylene, polyglycolic acid, polylactic acid, nylon, polyester, fluoropolymer, and copolymers or combinations thereof. See, e.g., U.S. Pat. Nos. 6,585,754 and 6,280,457 for a description of various polymers. Different components of the devices and assemblies may be made of different materials.

In embodiments in which the implantable device comprises an embolic coil, the main coil may be a coiled and/or braided structure comprising one or more metals or metal alloys, for example, Platinum Group metals, especially platinum, rhodium, palladium, rhenium, as well as tungsten, gold, silver, tantalum, stainless steel and alloys of these metals. Preferably, the device comprises a material that maintains its shape despite being subjected to high stress, for example, "super-elastic alloys" such as nickel/titanium alloys (48-58 atomic % nickel and optionally containing modest amounts of iron); copper/zinc alloys (38-42 weight % zinc); copper/zinc alloys containing 1-10 weight % of beryllium, silicon, tin, aluminum, or gallium; or nickel/aluminum alloys (36-38 atomic % aluminum). Particularly preferred are the alloys described in U.S. Pat. Nos. 3,174,851; 3,351,463; and 3,753,700. Especially preferred is the titanium/nickel alloy known as "nitinol." The main coil may also comprise a shape memory polymer such as those described in International Publication WO 03/51444. The implantable device is preferably electrically insulated, for example, by coating a metallic coil (e.g., stainless steel, platinum) with one or more electrically insulating materials, for example one or more polymers such as polyimide.

The implantable device may also change shape upon release from the deployment mechanism (e.g., pusher wire), for example change from a linear form to a relaxed, three-dimensional configuration upon deployment.

The devices described herein may also comprise additional components, such as co-solvents, plasticizers, coalescing solvents, bioactive agents, antimicrobial agents, antithrombogenic agents (e.g., heparin), antibiotics, pigments, radiopacifiers and/or ion conductors which may be coated using any suitable method or may be incorporated into the element(s) during production. See, e.g., U.S. Pat. No. 6,585,754 and WO 02/051460, U.S. Pat. No. 6,280,457. The additional components can be coated onto the device and/or can be placed in the vessel prior to, concurrently or after placement of one or more devices as described herein.

The devices described herein are often introduced into a selected site using the procedure outlined below. This procedure may be used in treating a variety of maladies. For instance in the treatment of an aneurysm, the aneurysm itself will be filled (partially or fully) with the compositions described herein.

Conventional catheter insertion and navigational techniques involving guidewires or flow-directed devices may be used to access the site with a catheter. The mechanism will be such as to be capable of being advanced entirely through the catheter to place vaso-occlusive device at the target site but yet with a sufficient portion of the distal end of the delivery mechanism protruding from the distal end of the catheter to enable detachment of the implantable vaso-occlusive device. For use in peripheral or neural surgeries, the delivery mechanism will normally be about 100-200 cm in length, more normally 130-180 cm in length. The diameter of the delivery mechanism is usually in the range of 0.25 to about 0.90 mm. Briefly, occlusive devices (and/or additional components) described herein are typically loaded into a carrier for introduction into the delivery catheter and introduced to the chosen site using the procedure outlined below. This procedure may be used in treating a variety of maladies. For instance, in treatment of an aneurysm, the aneurysm itself may be filled with the embolics (e.g. vaso-occlusive members and/or liquid embolics and bioactive materials) which cause formation of an emboli and, at some later time, is at least partially replaced by neovascularized collagenous material formed around the implanted vaso-occlusive devices.

A selected site is reached through the vascular system using a collection of specifically chosen catheters and/or guide wires. It is clear that should the site be in a remote site, e.g., in the brain, methods of reaching this site are somewhat limited. One widely accepted procedure is found in U.S. Pat. No. 4,994,069 to Ritchart, et al. It utilizes a fine endovascular catheter such as is found in U.S. Pat. No. 4,739,768, to Engelson. First of all, a large catheter is introduced through an entry site in the vasculature. Typically, this would be through a femoral artery in the groin. Other entry sites sometimes chosen are found in the neck and are in general well known by physicians who practice this type of medicine. Once the introducer is in place, a guiding catheter is then used to provide a safe passageway from the entry site to a region near the site to be treated. For instance, in treating a site in the human brain, a guiding catheter would be chosen which would extend from the entry site at the femoral artery, up through the large arteries extending to the heart, around the heart through the aortic arch, and downstream through one of the arteries extending from the upper side of the aorta. A guidewire and neurovascular catheter such as that described in the Engelson patent are then placed through the guiding catheter. Once the distal end of the catheter is positioned at the site, often by locating its distal end through the use of radiopaque marker material and fluoroscopy, the catheter is cleared and/or flushed with an electrolyte solution.

Once the selected site has been reached, the vaso-occlusive device is extruded by application of energy which degrades (melts) the polymer component of the detachment mechanisms as described herein. Upon melting of the polymer component, the implantable device is released in the desired position of the selected site.

Modifications of the procedures and assemblies described above, and the methods of using them in keeping with this disclosure will be apparent to those having skill in this mechanical and surgical art. These variations are intended to be within the scope of the claims that follow.

What is claimed is:

1. An assembly for delivering an implantable device in a body, comprising:
   an implantable device;
   a delivery device, with first and second electrically conductive members extending distally from the delivery device, wherein the first electrically conductive members comprises a distal end terminating in a first distinct ring structure and the second electrically conductive member comprises a distal end terminating in a second distinct ring structure, wherein first and second distinct ring structures are spaced apart from one another; and
   a composite detachment mechanism comprising a polymer strand secured to the implantable device, the polymer strand comprising a detachment portion coated with an electrically conductive material and threading through the first and second distinct ring structures and between the first and second electrically conductive members, such that energy conducted from the first conductive member to the second conductive member via the electrically conductive coating material heats and melts the detachment portion of the polymer strand to release the implantable device from the delivery device.

2. The assembly of claim 1, wherein the polymer comprises a low melt polymer.

3. The assembly of claim 2, wherein the low melt polymer is selected from the group consisting of polyethylene (PE), poly-L-lactic acid (PLLA), polyglycolic acid (PGA), polyvinyl alcohol (PVA) and combinations thereof.

4. The assembly of claim 1, wherein the conductive coating material comprises nickel, iron chromium, tin, gold, platinum or combinations thereof.

5. The assembly of claim 1, wherein the conductive coating comprises a single layer of one or more conductive materials.

6. The assembly of claim 1, wherein the conductive coating comprises multiple layers of two or more conductive materials.

7. The assembly of claim 1, further comprising an energy source operably connected to the first and second conductive members.

8. The assembly of claim 1, wherein the delivery device comprises a catheter, a guide wire, or a continuous conduit.

9. The assembly of claim 1, further comprising an insulating material.

10. The assembly of claim 1, wherein the implantable device comprises a vaso-occlusive device.

11. The assembly of claim 10, wherein the vaso-occlusive device is a coil or a tubular braid.

12. The assembly of claim 10, wherein the vaso-occlusive device comprises a metal.

13. The assembly of claim 12, wherein the metal is selected from the group consisting of gold, platinum, tungsten, nickel, titanium and alloys thereof.

14. The assembly of claim 10, wherein the vaso-occlusive device comprises a polymer.

15. The assembly of claim 14, wherein the vaso-occlusive device comprises a metal and the polymer is coated onto the metal.

* * * * *